United States Patent [19]

Ball et al.

[11] Patent Number: 6,162,911
[45] Date of Patent: Dec. 19, 2000

[54] CRYSTALLINE IMIDAZOLE COMPLEXES AS CARBAPENEM INTERMEDIATES AND SYNTHESIS

[75] Inventors: Richard G. Ball, Edison; Nancy N. Tsou, Westfield; James A. Mc Cauley, Belle Mead; Chunhua Yang, Edison; Nobuyoshi Yasuda, Mountainside, all of N.J.

[73] Assignee: Merck & Co., Inc., Rahway, N.J.

[21] Appl. No.: 09/133,201

[22] Filed: Aug. 13, 1998

Related U.S. Application Data

[60] Provisional application No. 60/058,215, Sep. 9, 1997.

[51] Int. Cl.[7] .................................................. C07D 205/08

[52] U.S. Cl. ............................................................ 540/200

[58] Field of Search ............................................. 540/200

[56] References Cited

PUBLICATIONS

Y. Nagao et al., *J. Org. Chem*, 57, pp. 4243–4349 (1992).
S. M. Schmitt et al. J. Antibiotic, 41(6), pp. 780–787 (1988).

*Primary Examiner*—Mark L. Berch
*Attorney, Agent, or Firm*—James M. Hunter, Jr.; Mark R. Daniel

[57] ABSTRACT

Novel crystalline carbapenem intermediate compounds of formula I:

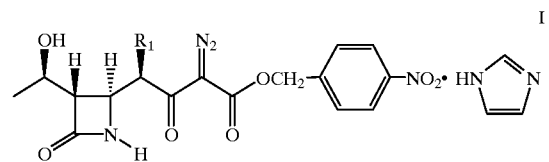

wherein:

$R_1$ represents $CH_3$ or H and an efficient process for synthesis thereof are described.

10 Claims, 2 Drawing Sheets

CRYSTALLINE IMIDAZOLE COMPLEXES AS CARBAPENEM INTERMEDIATES AND SYNTHESIS

This application claims the benefit of U.S. provisional Application Ser. No. 60/058,215, filed Sep. 9, 1997.

BACKGROUND OF THE INVENTION

The present invention relates to crystalline intermediate compounds useful in the synthesis of carbapenem antibiotics. The carbapenems derived from the present invention are useful against gram positive microorganisms, especially Methicillin resistant Staphylococcus aureus (MRSA), Methicillin resistant Staphylococcus epidermidis (MRSE), and Methicillin resistant coagulase negative Staphylococci (MRCNS). There is an increasing need for carbapenems effective against such pathogens, as well as intermediates which facilitate their production. The crystalline intermediates of the present invention thus facilitate an important contribution to therapy for treating infections caused by these difficult to control pathogens.

SUMMARY OF THE INVENTION

The present invention relates to a process for preparation of a crystalline complex represented by structural formula I:

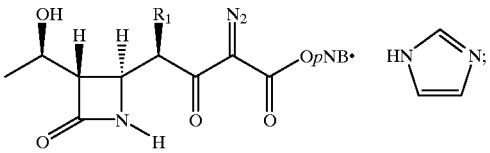

I wherein:

$R_1$ represents $CH_3$ or H;

comprising reacting a compound of formula II:

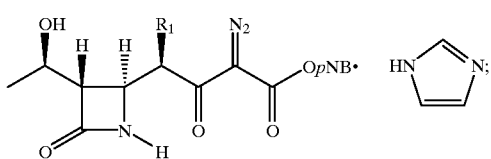

II wherein $R_1$ is defined above;

with irnidazole in the presence of a solvent to yield the crystalline complex formula I and purification and isolation of a compound of formula I.

This process is an efficient and facile pathway for preparing stable crystalline carbapenem intermediates. This process also leads to a new crystalline complex which is easy to purify.

The present invention also relates to the crystalline compound of formula I:

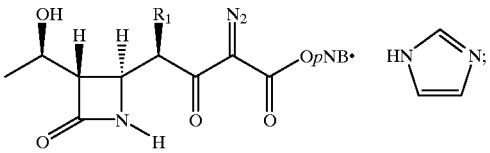

I wherein:

$R_1$ represents $CH_2$ or H and pNB is.

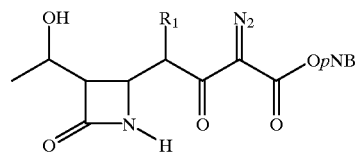

This novel compound is a stable and storable crystalline solid.

BRIEF DESCRIPTION OF THE DRAWINGS

The invention is described in connection with the following drawings in which.

DETAILED DESCRIPTION OF THE INVENTION

Some of the intermediates of the present invention occur as geometric isomers. The process of synthesizing all such isomers is encompassed by the present invention.

In a preferred aspect of this invention, $R_1$ is methyl ($CH_3$).

The invention is described herein in detail, using the terms defined below unless otherwise specified.

pNB refers to the p-nitrobenzyl.

Compound II is commercially available or may be synthesized according to the general methods disclosed in, for example, Nagao, et al., JOCEAH; J. Org. Chem., EN; 57; 15; 1992; 4243–4249: See also Schmitt, et al., J. Antibiotics 41 (6):780–787 (1988).

Suitable solvents include hydrocarbons such as hexane(s), heptene(s) and pentene(s) and the like; ethers such as diethyl ether, t-butylmethylether, tetrahydrofuran (THF) and the like; esters such as methyl acetate, ethyl acetate, propyl acetate, isopropylacetate, butyl acetate and the like; toluene, benzene, chlorobenzene, xylene, dimethylformamide (DMF), dimethylsulfoxide (DMSO), N,N-dimethylacetamide (DMAC), 1-ethyl-2-pyrrolidinone, 1-methyl-2-pyrrolidinone, methylene chloride, dichloroethane, chloroform, acetone, methylethyl ketone, alcohols such as methanol, ethanol, propanol, isopropyl alcohol, butanol, amyl alcohol and the like; and any combination thereof, preferably isopropyl acetate, isopropyl acetate/hexane(s), isopropyl acetate/hexane(s)/toluene, or isopropyl acetate/THF.

Figure 1:
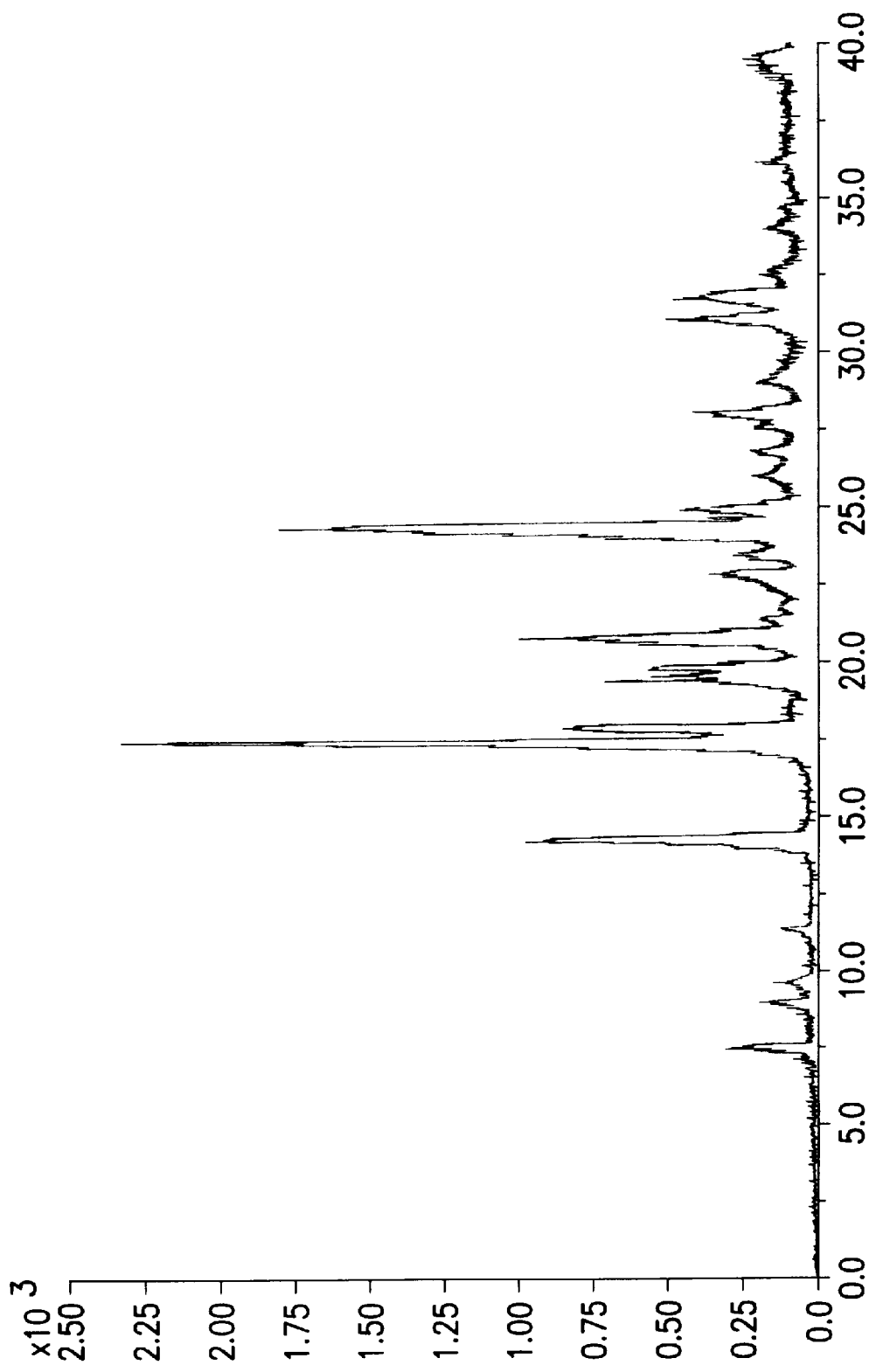
FIG. 1: X-ray crystallography pattern of compound I.
Figure 2:
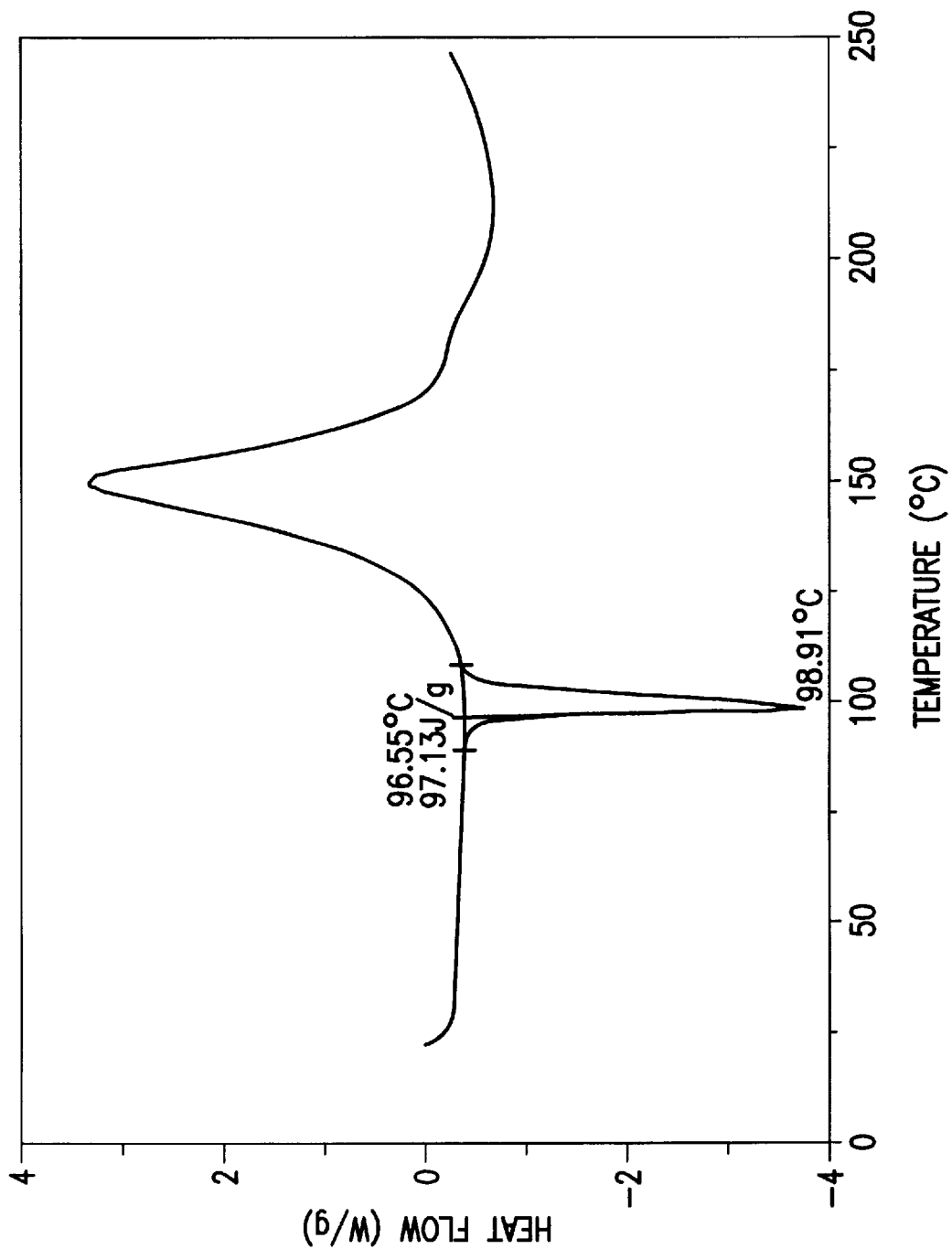
FIG. 2: Differential Scanning Calorimetric Cell (DSC) thermogram of compound I.

The compounds of the present invention may be isolated in various crystal forms, such as that illustrated by FIGS. 1 and 2. This encompasses compounds of stable crystal structure, and is not limited to the crystal form described in the example.

Generally, crystallization can be conducted in a solvent such as isopropyl acetate. Added to this is a compound of formula II and the imidazole in about a 1 to about 2 mole equivalent ratio of compound II to imidazole, preferably about a 1 to about a 1.2 mole equivalent ratio. A crystalline complex is formed by seeding in appropriate solvent mixture at about −10° C. to about 40° C., preferably at about 0° C. to about 10° C.

The present invention is illustrated by the following non-limiting example.

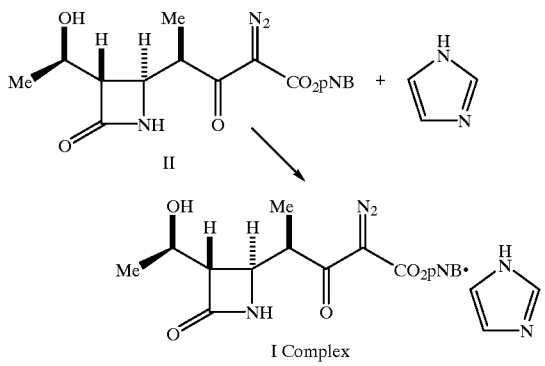

I Complex

To a 250 ml 3-neck flask equipped with a thermocouple and a nitrogen inlet was added isopropyl acetate (70 ML), compound II (7.5 g; 19.2 mmol) and imidazole (1.6 g; 23.0 mmol). The resulting slurry was stirred at 40° C. for 10 minutes. At 30° C., crystal seeds were added. After the mixture was cooled down to ambient temperature, hexanes (30 ml) was slowly added to the mixture. After aging 1 hr at 0° C., crystals were filtered, washed with isopropyl acetate/hexane (20 v/v %; 30 mL), and dried under a nitrogen stream to give imidazole complex as colorless crystals (8.65 g). NMR spectroscopy yielded the following results: $^1$H NMR (250 MHz, $CDCl_3$): δ 8.24 (m, J=8.7 Hz, 2H), 7.66 (s, 1H), 7.52 (d, J=8.6 Hz, 2H), 7.07 (s, 2H), 6.50 (s, 1H), 5.81 (broad s, 2H), 5.34 (s, 2H), 4.12 (quintets, J=6.5 Hz, 1H), 3.85 (dd, J=6.3 and 2.0 Hz, 1H), 3.75 (quintets, J=6.7 Hz, 1H), 2.89 (dd, J=7.0 and 2.0 Hz, 1H), 1.28 (d, J=6.3 Hz, 3H), 1.20 (d, J=6.9 Hz, 3H) $^{13}$C NMR (62.9 MHZ, $CDCl_3$): δ 8 194.8, 168.1, 160.4, 148.0, 141.9, 135.1, 128.8, 124.0, 121.9, 76.0, 65.7, 65.6, 62.0, 53.3, 45.0, 21.1, 13.4.

The melting point was measured using DSC thermography. The DSC instrument was a TA Instrument DSC 9210 and the DSC curve run at a heating rate of 10° C./min under a nitrogen flow of about 30 mL/min from room temperature to 250° C. A major endotherm (melting endotherm) was detected with a peak temperature of about 99° C., an extrapolated onset temperature of 97° C. and a heat of melting of 97 Joules/gm. (See FIG. 2).

The X-ray crystallography was conducted using a Phillips APD3720 using CuKa radiation. The powder pattern was run at 0.075 2-θ/sec from about 2 to about 40 2-θ. The x-ray crystallography pattern yielded the results summarized in FIG. 1 and Table 1, below.

TABLE 1

| Angle (2-theta) | d-spacing (Ang) | Rel. Intensity (%) |
|---|---|---|
| 7.57 | 11.7 | 14 |
| 9.03 | 9.79 | 9 |
| 9.70 | 9.12 | 5 |
| 11.40 | 7.76 | 5 |

TABLE 1-continued

| Angle (2-theta) | d-spacing (Ang) | Rel. Intensity (%) |
|---|---|---|
| 14.30 | 6.19 | 40 |
| 17.53 | 5.06 | 100 |
| 18.00 | 4.92 | 35 |
| 19.50 | 4.55 | 30 |
| 19.97 | 4.44 | 20 |
| 20.60 | 4.31 | 19 |
| 20.9 | 4.25 | 44 |
| 22.93 | 3.87 | 14 |
| 23.51 | 3.78 | 11 |
| 24.46 | 3.64 | 84 |
| 24.94 | 3.57 | 18 |
| 28.12 | 3.17 | 16 |
| 31.19 | 2.87 | 18 |
| 31.88 | 2.81 | 21 |

What is claimed is:

1. A process for preparation of a crystalline complex of formula I:

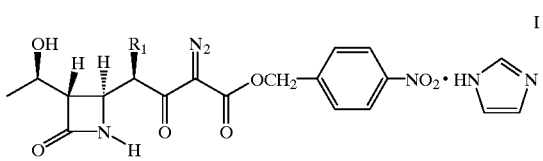

wherein:

$R_1$ represents $CH_3$ or H;

comprising reacting a compound of formula II:

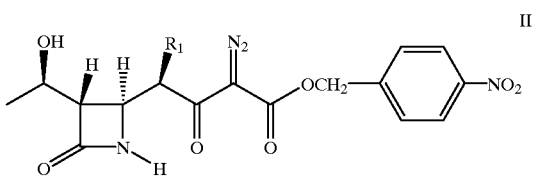

with imidazole in the presence of a solvent to yield the compound of formula I and purification and isolation of a compound of formula I.

2. A process according to claim 1 wherein the solvent is selected from the group consisting of hydrocarbons selected from hexane(s), heptene(s) and pentene(s); ethers such as diethyl ether, t-butylmethylether, tetrahydrofuran; esters such as methyl acetate, ethyl acetate, propyl acetate, isopropylacetate, butyl acetate; toluene, benzene, chlororbenzene, xylene, dimethylformamide, dimethylsulfoxide, N,N-dimethylacetamide, 1-ethyl-2-pyrrolidinone, 1-methyl-2-pyrrolidinone, methylene chloride, dichloroethane, chloroform, acetone, methylethyl ketone, methanol, ethanol, propanol, isopropyl alcohol, butanol, amyl alcohol; and any combination thereof.

3. A process according to claim 2 wherein the solvent is isopropyl acetate, isopropyl acetate/hexane(s), isopropyl acetate/hexane(s)/toluene, or isopropyl acetate/THF.

4. A process according to claim 1 wherein $R^1$ is methyl.

5. A process according to claim 1 wherein the mole ratio of compound II to imidazole is about 1 to about 2.

6. A process according to claim 5 wherein the mole ratio of compound II to imidazole is about 1 to about 1.2.

7. A process according to claim 1 wherein the reaction is carried out at a temperature of about about −10° C. to about 40° C.

8. A process according to claim 7 wherein the reaction is carried out at a temperature of about 0° C. to about 10° C.

9. A crystalline complex of formula I:

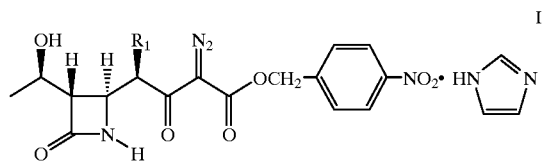

wherein:

$R_1$ represents $CH_3$ or H.

10. The compound of claim 7 wherein $R_1$ represents $CH_3$.

* * * * *